US00PP16446P3

(12) United States Plant Patent
Ikuma

(10) Patent No.: US PP16,446 P3
(45) Date of Patent: Apr. 18, 2006

(54) ***CUPRESSUS MACROCARPA* PLANT NAMED 'EMERALD CREST'**

(50) Latin Name: *Cupressess macrocarpa*
Varietal Denomination: Emerald Crest

(76) Inventor: Masanari Ikuma, 15916 29th Dr. SE., Mill Creek, WA (US) 98012

( * ) Notice: Subject to any disclaimer, the term of this patent is extended or adjusted under 35 U.S.C. 154(b) by 138 days.

(21) Appl. No.: 10/704,108

(22) Filed: Nov. 7, 2003

(65) Prior Publication Data

US 2005/0102724 P1 May 12, 2005

(51) Int. Cl.
*A01H 4/00* (2006.01)

(52) U.S. Cl. ..... Plt./213

(58) Field of Classification Search ..... Plt./213
See application file for complete search history.

*Primary Examiner*—Anne Marie Grunberg
(74) *Attorney, Agent, or Firm*—DWC Law Firm, P.S.

(57) ABSTRACT

A new and distinct variety of *Cupressus macrocarpa* plant characterized by coloration comprising light green patches among an overall darker green color.

5 Drawing Sheets

I. BACKGROUND OF THE INVENTION

The present invention relates to a new and distinct variety of *Cupressus macrocarpa* discovered by Masanari Ikuma. This cultivar sported from a *Cupressus macrocarpa* 'Wilma Goldcrest' and is referred to as 'Emerald Crest'. It was not the result of a breeding program.

The parent 'Wilma Goldcrest', is a slow growing conifer that is known to reach a maximum height of about six (6) to nine (9) feet. The parent is typically pyramidal, or conical in shape at early stages in its growth. At later stages of growth, the 'Wilma Goldcrest' maintains substantially similar conical shape with denser branching. The leaves or foliage of the 'Wilma Goldcrest' are colored light green to yellow-green.

The new cultivar 'Emerald Crest' is distinct from its parent in coloration throughout the period observed. At earlier stages of growth (i.e. at about six (6) months old), the foliage of 'Emerald Crest' is predominantly darker green in comparison with the light-green or green-yellow 'Wilma Goldcrest'. The 'Emerald Crest' also has lighter green sections that are noticeable and tend to appear like light green patches to the human eye against the contrast of the predominantly darker green color of this new plant.

*Cupressus macrocarpa* 'Emerald Crest' has been asexually reproduced by the inventor using vegetative cutting (cutting of the stems) since at least October 2000. These efforts by the inventor have shown that the plant reproduces true to the type in successive generations and the distinctive characteristics of the new plant remain stable.

II. BRIEF SUMMARY OF THE INVENTION

The cultivar, *Cupressus macrocarpa* 'Emerald Crest' has distinguishing color characteristics in comparison to the *Cupressus macrocarpa* 'Wilma Goldcrest' from which it sported. These distinguishing color characteristics include a broader range of colors in the foliage of the new cultivar. For example, while the 'Wilma Goldcrest' consists of shades of lighter-green, the majority of foliage of the 'Emerald Crest' is darker green (the terms "darker green" and "lighter green" are used herein only to describe the relative shades of green) with sections of lighter-green colors. The sections of lighter-green colors on the 'Emerald Crest' tend to contrast with the darker green colors of the plant giving the 'Emerald Crest' an appearance of having patches. The lighter-green patches are substantially similar in color to the lighter-green green colors of the 'Wilma Goldcrest'.

III. BRIEF DESCRIPTION OF THE FIGURES

The colors shown are as true as is reasonably possible to obtain by conventional photographic procedures. Both digital and conventional photographs are illustrated in FIGS. 1–5.

IV. DETAILED BOTANICAL DESCRIPTION

Some colors are described, infra, with reference to The Royal Horticultural Society ("R.H.S.") Colour Chart. In other instances, color descriptions are set forth in ordinary terms where appropriate, such as in describing one color relative to another (e.g., "darker green" and "lighter green"). The terms "darker green" and "lighter green" are not specific color references, such as that of The R.H.S. Colour Chart, but instead only describe shades of green in relation to one another. This plant is not the result of federally sponsored research or development.

This new variety of *Cupressus macrocarpa* was found as a sport of *Cupressus macrocarpa* 'Wilma Goldcrest'. The new variety, 'Emerald Crest' was first discovered in August 2000, in green houses in Snohomish, Wash. Like its parent, the 'Emerald Crest' takes on an upright pyramidal or conical form at early stages of growth and maintains a similar shape throughout the growth cycle observed. The new cultivar is a slow growing conifer, like its parent.

Figure 1:
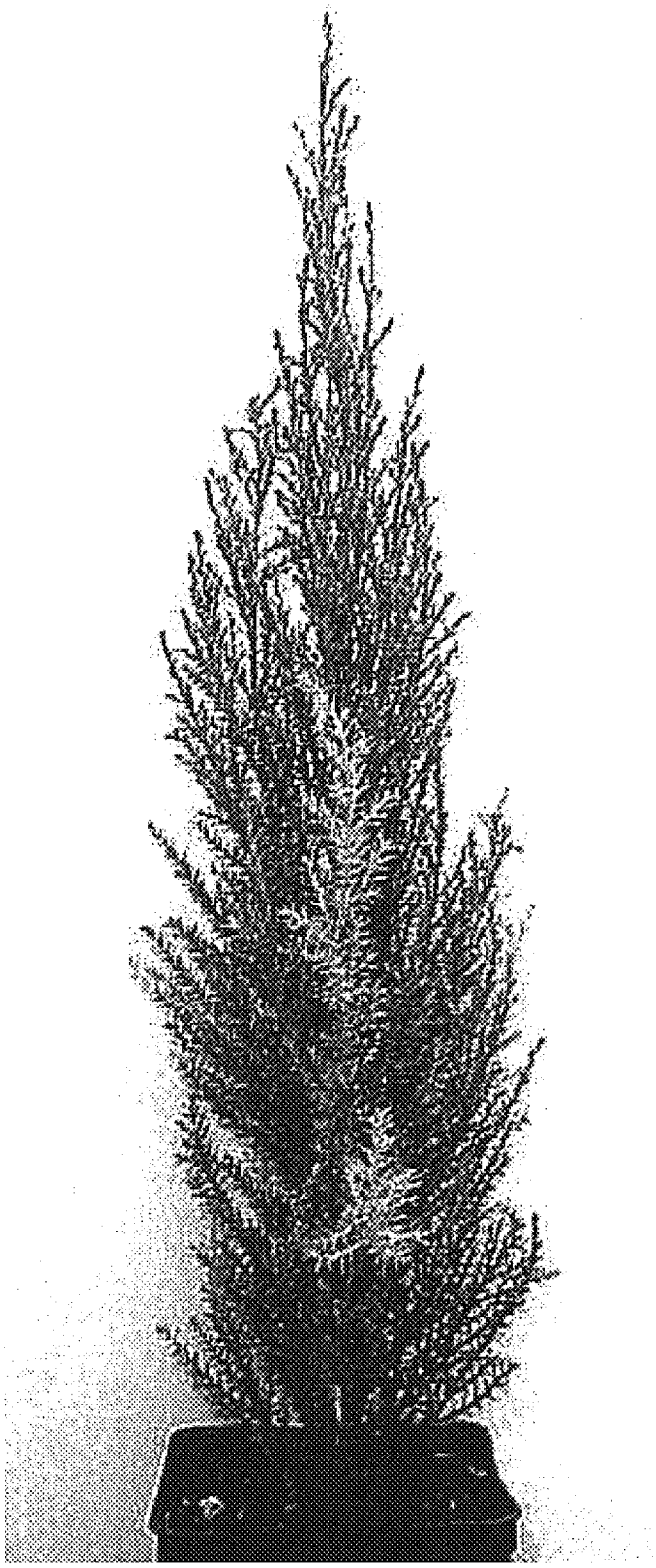
FIG. 1 is a digital photograph of the 'Emerald Crest' at age eight (8) months with a pyramidal shape that is also typical of its parent, the 'Wilma Goldcrest'.
Figure 2:
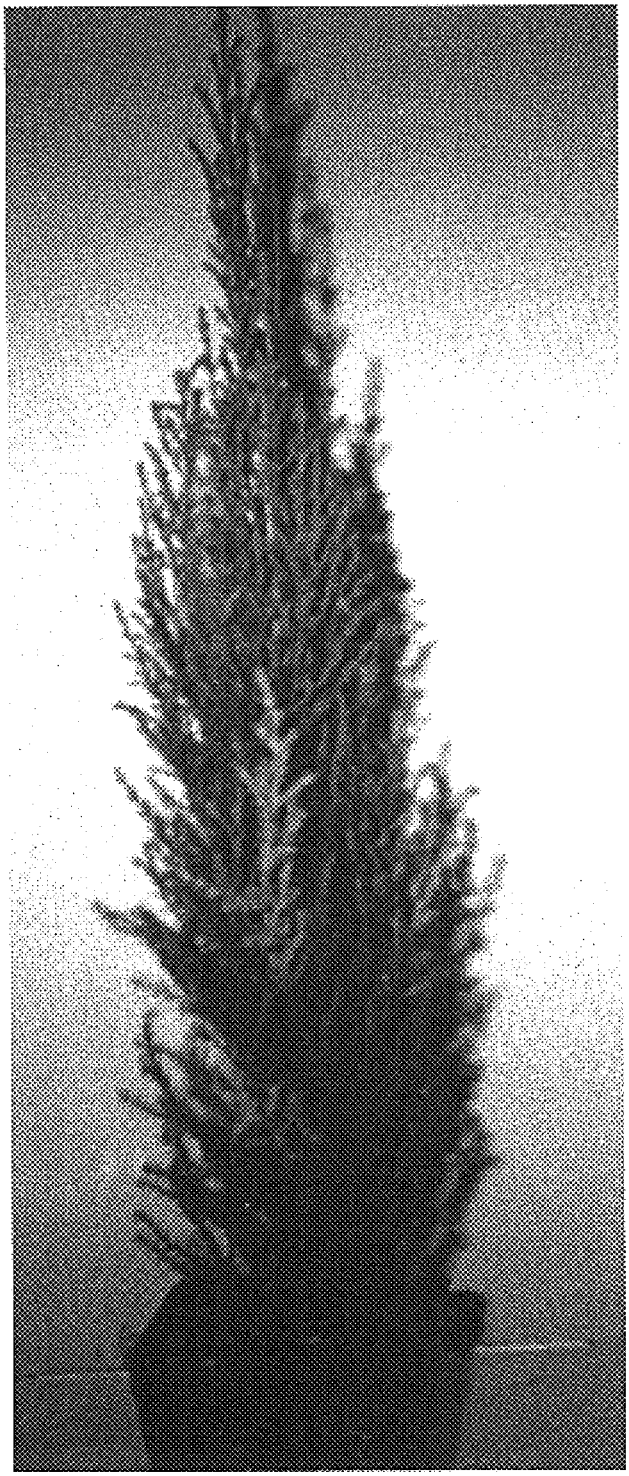
FIG. 2 is a conventional photograph of the plant of FIG. 1.
Figure 3:
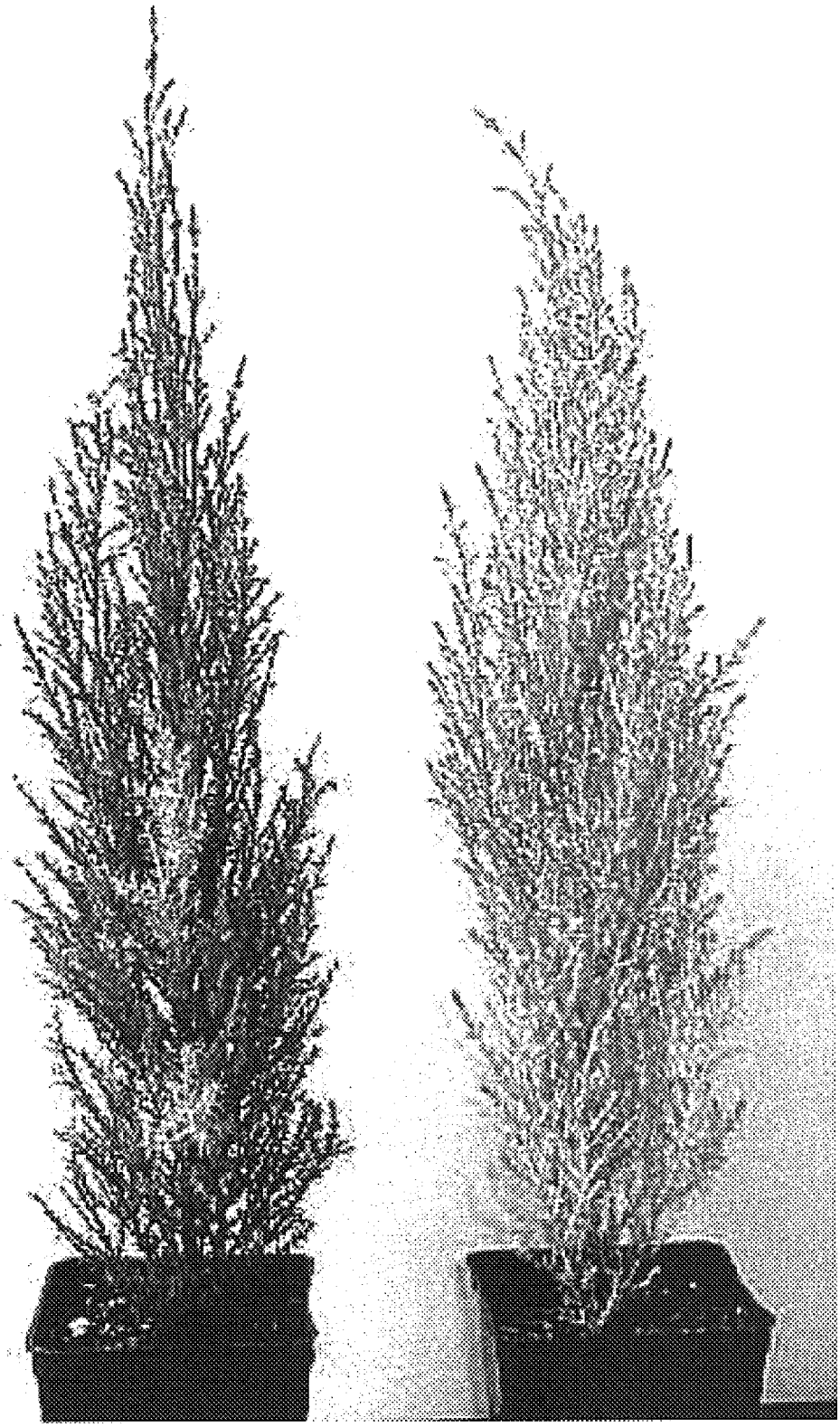
FIG. 3 is a digital photograph showing the 'Emerald Crest' of FIG. 1 and FIG. 2 along with its parent, *Cupressus macrocarpa* 'Wilma Goldcrest', positioned to the right of the 'Emerald Crest'.
Figure 4:
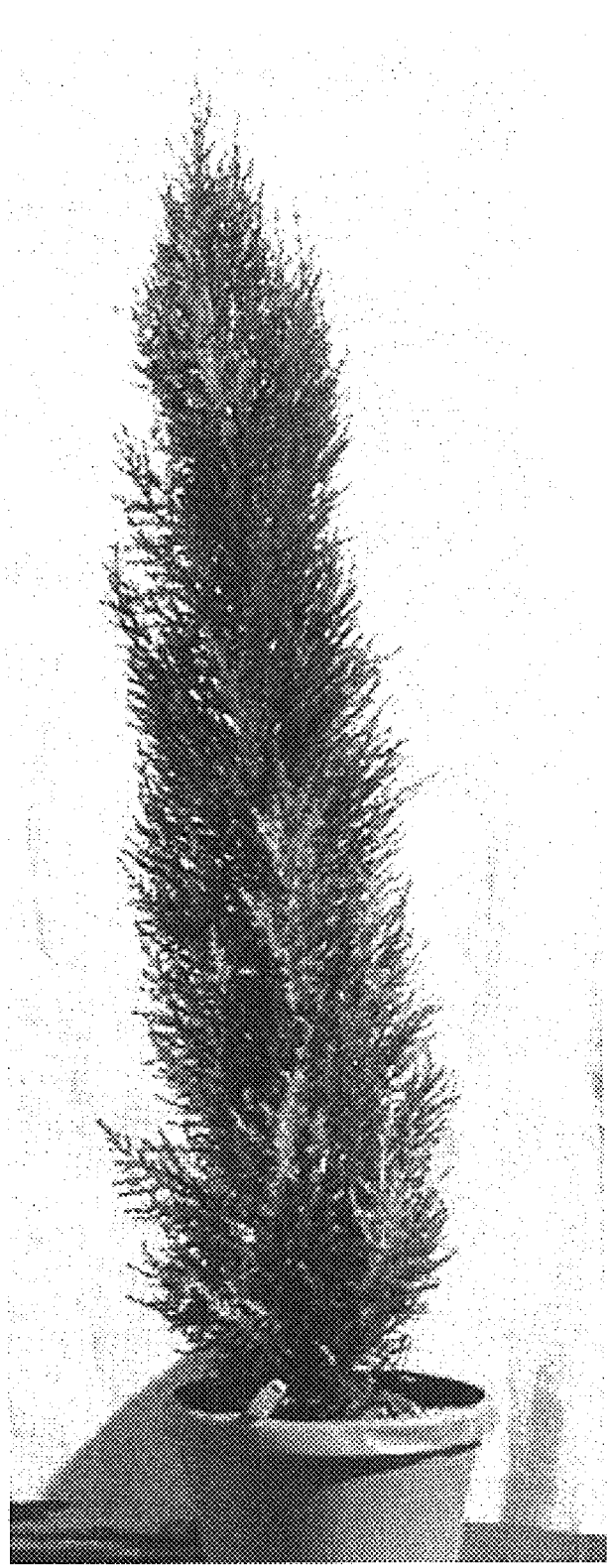
FIG. 4 is a conventional photograph showing another 'Emerald Crest' at about age two (2) years.
Figure 5:
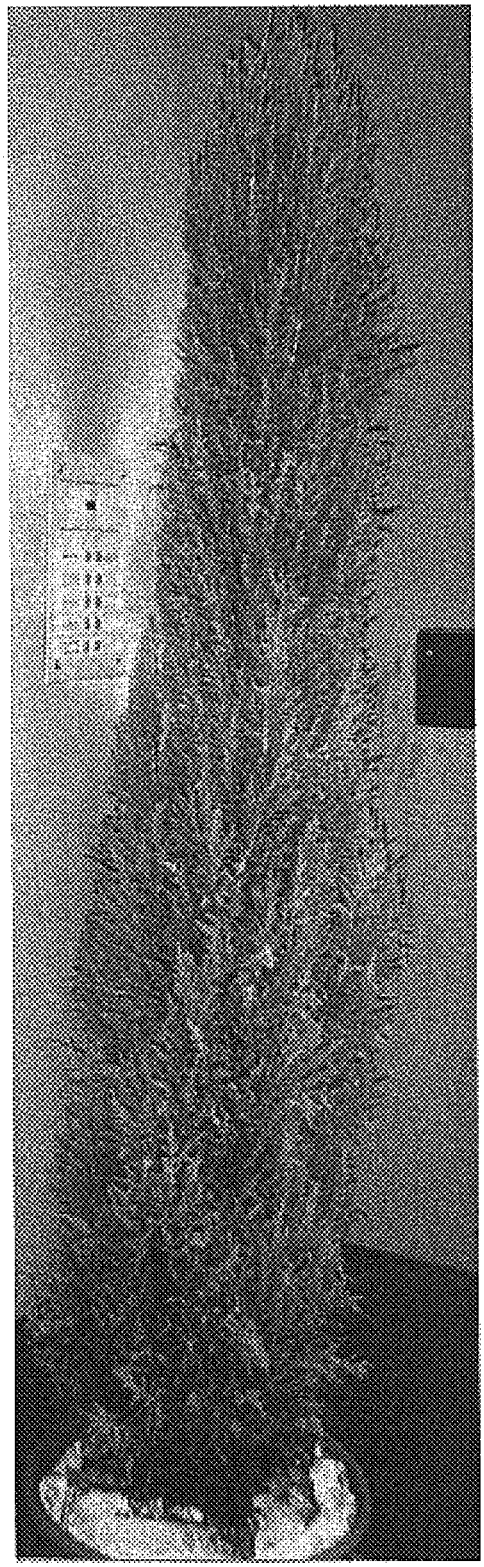
FIG. 5 is a conventional photograph showing an 'Emerald Crest' at about age three (3) years with a pyramidal shape that is also typical of the 'Wilma Goldcrest' at same or similar stages of growth.

Of the three new cultivars illustrated in FIGS. 1–5, the ages were eight (8) months, FIGS. 1–3, two (2) years, FIG. 4, and three (3) years, FIG. 5 at the time the photographs were taken.

The bark of each of the illustrated plants is brown. The leaves of this new variety of plant, like those of its parent, are small, partially pressed against its shoots at their base, and scale-like. Their widths are approximately 1/32" to 3/32" with lengths of about 1/16" to 3/16" inch long. Among the distinguishing characteristics of the new plant is its color. The colors of the leaves or foliage of this new variety are wider in range than its parent, the 'Wilma Goldcrest'. A major portion of 'Emerald Crest's' foliage is darker-green in comparison with the lighter green color of the 'Wilma Goldcrest'. At early stages of growth (approximately 6–8 months), the darker-green of the 'Emerald Crest' is Green Group 132B in the summer. See FIGS. 1–3. At this time, the 'Emerald Crest' also displays distinctive lighter shades of green on its foliage, mixed in with the darker-green foliage. The lighter shades of green (Green Group 142C in summer) have the appearance of patches of lighter color spilled in among the darker green foliage. It is also notable that these lighter shades of green on the 'Emerald Crest' are positioned at end portions of the plant's branches and shoots, and extend inward therefrom, toward darker green portions of the plant. See FIGS. 1–5.

The branch bark and trunk bark of the new plant is fibrous. Branch texture is course. Bark color in branches and trunk of the oldest observed plant at the time of this application was brownish. The leaves and bark are observed to be lemon scented. The leaves are scale-like, and elongated with pointed ends.

No significant differences have been observed between the 'Emerald Crest' and its parent 'Wilma Goldcrest' in fragrance, taste, disease resistances, productivity, precocity, or vigor.

The oldest specimen of 'Emerald Crest' was found in August 2000. See FIG. 5. At three (3) years of age, its shape, form and dimensions are similar to those of a 'Wilma Goldcrest' at the same age. The following data are from measurements of the three year-old specimen that was asexually reproduced under greenhouse conditions in Snohomish, Wash., USA, during August 2000.

Overall form: Upright pyramidal.
Overall height: 67 inches.
Trunk diameter at widest point: 1.5 inches at 4 inches above ground.
Growth habit: Dense and pyramidal. Slow growth under normal fertilization and moisture conditions. Branches rise at about 45 degrees from vertical axis.
Foliage: Leaves are small, partially pressed against the shoots of the plant at their base, and scale-like. Widths of the leaves are approximately 1/32" to 3/32" with lengths of about 1/16" to 3/16" inch long.

The three (3) year old 'Emerald Crest' of FIG. 5 differs in coloration from the younger plant illustrated in FIGS. 1–3. First, the three (3) year old plant retains its predominantly darker green color in contrast with the lighter green of the 'Wilma Goldcrest' at comparable age. However, the darker green color foliage at three (3) years is as dark as Green Group 132A in the summer. Lighter green portions remain randomly positioned about the three (3) year old new plant, just as in its early stages of growth. However, the lighter green portions in the three (3) year old plant are Green Group 144D in the summer. Also, the lighter green portions are more evenly and proportionally distributed about the plant at this age than at early stages.

What is claimed is:

1. A new, distinct and unique variety of *Cupressesus macrocarpa* plant named 'Emerald Crest' substantially as illustrated and described herein.

* * * * *